(12) United States Patent
Wada

(10) Patent No.: US 9,655,541 B2
(45) Date of Patent: May 23, 2017

(54) BIOSIGNAL MEASUREMENT APPARATUS

(75) Inventor: Seiji Wada, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 160 days.

(21) Appl. No.: 14/235,493

(22) PCT Filed: Sep. 3, 2012

(86) PCT No.: PCT/JP2012/005569
§ 371 (c)(1),
(2), (4) Date: Jan. 28, 2014

(87) PCT Pub. No.: WO2013/042322
PCT Pub. Date: Mar. 28, 2013

(65) Prior Publication Data
US 2014/0187997 A1    Jul. 3, 2014

(30) Foreign Application Priority Data

Sep. 21, 2011  (JP) .................................. 2011-205582

(51) Int. Cl.
*A61B 5/0476*    (2006.01)
*A61B 5/0402*    (2006.01)
(Continued)

(52) U.S. Cl.
CPC .......... *A61B 5/0476* (2013.01); *A61B 5/6814* (2013.01); *A61B 5/024* (2013.01); *A61B 5/0402* (2013.01)

(58) Field of Classification Search
CPC .... A61B 5/0476; A61B 5/0482; A61B 5/0402
(Continued)

(56) References Cited

U.S. PATENT DOCUMENTS 3,732,859 A * 5/1973 Tateno ................. A61B 5/0424
  600/544
2008/0243013 A1* 10/2008 Yanai ................. A61B 5/04288
  600/509
2009/0043221 A1* 2/2009 Kaplan ................. A61B 5/6843
  600/544

FOREIGN PATENT DOCUMENTS

JP    63-314473    12/1988
JP    63314473 A * 12/1988
(Continued)

OTHER PUBLICATIONS

Sexena, A., Ray, S., and Varma, R.K. A Novel Electric Shock Protection System Based on Contact Currents on Skin Surface. NPSC, 2002, pp. 584-587.*
(Continued)

*Primary Examiner* — Michael C Stout
*Assistant Examiner* — Nicholas E Kolderman
(74) *Attorney, Agent, or Firm* — Chip Law Group

(57) ABSTRACT

A biosignal measurement apparatus according to the present technology includes a voltage supply, a measurement electrode, a resistor, a first amplifier, and a neutral electrode. The measurement electrode is connected to the voltage supply and brought into contact with a living body. The resistor is connected between the voltage supply and the measurement electrode. The first amplifier amplifies a potential between the resistor and the measurement electrode. The neutral electrode is brought into contact with the living body. The object of the invention is to provide a biosignal measurement apparatus capable of measuring a contact resistance with high accuracy.

5 Claims, 3 Drawing Sheets

(51) Int. Cl.
  *A61B 5/00*    (2006.01)
  *A61B 5/024*    (2006.01)
(58) Field of Classification Search
  USPC .......................................................... 600/547
  See application file for complete search history.

(56)         References Cited

FOREIGN PATENT DOCUMENTS

JP         10-062463        3/1998
JP         2003-180647      7/2003

OTHER PUBLICATIONS

Rosell, Javier, et al. "Skin impedance from 1 Hz to 1 MHz." Biomedical Engineering, IEEE Transactions on 35.8 (1988): 649-651.*
International Search Report: Application No. PCT/JP2012/05569; Filed on Sep. 3, 2012. Completion of International Search Report: Nov. 27, 2012 (PCT/ISA/210).
Confidence of Digital Electroencephalograph "The Principle of Impedance Check" Sep. 25, 2012, Nihon Kohden Corporation.

* cited by examiner

US 9,655,541 B2

BIOSIGNAL MEASUREMENT APPARATUS

TECHNICAL FIELD

The present technology relates to a biosignal measurement apparatus for measuring a biosignal such as an electroencephalogram and an electrocardiogram.

BACKGROUND ART

In a biosignal measurement apparatus that measures a potential signal (hereinafter, referred to as biosignal) such as an electroencephalogram, an electromyogram, an electrocardiogram, and a body fat percentage by bringing a living body (animal including a human being) into contact with an electrode, a contact resistance exists between the electrode and a surface of the living body.

The contact resistance affects a biosignal detected by an electrode particularly in the case where a resistance value is large, so a surface of a living body and the contact surface of an electrode are generally coated with a conductive paste, for example, thereby reducing the contact resistance. However, it is difficult to completely eliminate the contact resistance, so the contact resistance is measured before a biosignal is measured.

For example, Non-Patent Document 1 discloses a digital electroencephalograph that applies an alternating-current signal to an electrode from an alternating-current voltage supply through a resistor to obtain a value of impedance (contact resistance) from a potential difference in the contact resistance. That is, in the digital electroencephalograph, the applied voltage is divided by the resistor and the contact resistance.

Non-Patent Document 1: "Secret of digital electroencephalograph" written by Kazuteru Yanagihara, (online), Kanto Study Group for Neurophysiological Tests (retrieved on Aug. 1, 2011)

SUMMARY OF INVENTION

Problem to be Solved by the Invention

However, in the digital electroencephalograph disclosed in Non-Patent Document 1, a high voltage of 10 V is supplied to the electrode through a high resistance of 100 MΩ. Generally, a contact resistance is approximately 10 KΩ, which is approximately one ten-thousandth of a resistance value of the resistor.

Therefore, the divided voltage by the contact resistance is significantly smaller than the divided voltage of the resistor and is easily affected by an error of the alternating-current voltage supply or the resistor. For example, even in the case where the resistor has an error of 1%, an error range becomes equal to or larger than the contact resistance, so it is thought that calibration has to be performed as necessary in order to measure the contact resistance with high accuracy.

In view of the circumstances as mentioned above, it is an object of the present technology to provide a biosignal measurement apparatus capable of measuring the contact resistance with high accuracy.

Means for Solving the Problem

To achieve the object mentioned above, according to an embodiment of the present technology, there is provided a biosignal measurement apparatus including a voltage supply, a measurement electrode, a resistor, and a first amplifier.

The measurement electrode is connected to the voltage supply and brought into contact with a living body.

The resistor is connected between the voltage supply and the measurement electrode.

The first amplifier amplifies a potential between the resistor and the measurement electrode.

With the structure described above, the voltage applied from the voltage supply is divided by the resistor and the contact resistance. The first amplifier detects the potential between the resistor and the measurement electrode, so it is possible to calculate the resistance value of the contact resistance from the partial pressure by the contact resistance.

The resistor may have a resistance value which is a logarithmic center value of a resistance value range intended to be measured in a resistance value range of a contact resistance between the measurement electrode and the living body.

As described above, the voltage applied from the voltage supply is divided by the resistor and the contact resistance. However, a resolution of the contact resistance differs depending on the resistance value of the resistor, and in the range, the logarithmic center value of which is the resistance value of the resistor, the highest resolution can be obtained. Thus, by setting the resistance value of the resistor to this value, it is possible to measure the contact resistance with high accuracy.

The resistance value range is a range from 10 KΩ to 1 MΩ, both inclusive, and the resistor may have the resistance value of 100 KΩ.

A general range of the contact resistance at a time when the measurement electrode is attached to the living body surface is set to the range from 10 KΩ to 1 MΩ. At this time, the resistance value of the resistor is set to 100 KΩ, thereby making it possible to measure the contact resistance in this range with high accuracy.

The biosignal measurement apparatus may further include a switch capable of opening and closing connection between the resistor and the measurement electrode.

With this structure, by turning off the switch, the application of the voltage from the voltage supply to the measurement electrode is stopped, and a potential signal (biosignal) generated in the living body can be detected.

The biosignal measurement apparatus may further include a second amplifier and a reference electrode brought into contact with the living body and connected to the second amplifier.

With this structure, the contact resistance can be measured for each electrode.

Effect of the Invention

As described above, according to the present technology, the object of the present technology of providing the biosignal measurement apparatus capable of measuring the contact resistance with high accuracy can be achieved.

BEST MODE(S) FOR CARRYING OUT THE INVENTION

First Embodiment

A biosignal measurement apparatus according to a first embodiment of the present technology will be described.

[Structure of Biosignal Measurement Apparatus]

Figure 1:
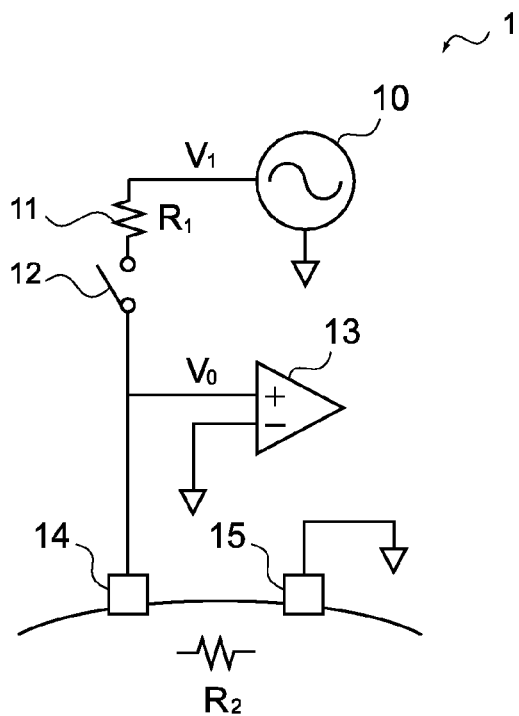
FIG. 1 A schematic diagram showing the structure of a biosignal measurement apparatus according to a first embodiment of the present technology.

FIG. 1 is a schematic diagram showing the structure of a biosignal measurement apparatus 1 according to this embodiment. The biosignal measurement apparatus 1 is an apparatus (electroencephalograph) that is connected to a scalp of a user and measures an electroencephalogram of the user but is not limited to this. The biosignal measurement apparatus 1 can be an apparatus capable of measuring a biosignal generated in a living body (animal including a human being), such as an electromyogram, an electrocardiogram, and a body fat percentage. As shown in the figure, the biosignal measurement apparatus 1 includes a voltage supply 10, a resistor 11, a switch 12, an amplifier 13, a measurement electrode 14, and a neutral electrode 15.

The voltage supply 10 is connected to the resistor 11, and the resistor 11 is connected to the switch 12. The switch 12 is connected to the measurement electrode 14, and the amplifier 13 is connected between the switch 12 and the measurement electrode 14. The neutral electrode 15 is connected to a ground. As shown in the figure, the measurement electrode 14 and the neutral electrode 15 are attached to the scalp of the user and electrically connected thereto through a conductive paste or the like.

For the voltage supply 10, a general alternating-current voltage supply can be used. A frequency and a voltage are not particularly limited. For example, the frequency can be set to 10 Hz, and a voltage amplitude can be set to ±500 µV. Hereinafter, an applied voltage by the voltage supply 10 is represented by $V_1$.

The resistor 11 divides the applied voltage with a contact resistance (to be described later). Hereinafter, a resistance value of the resistor 11 is represented by $R_1$. The resistance value $R_1$ will be described later in detail.

The switch 12 makes it possible to open and close a circuit. In the biosignal measurement apparatus 1, by opening and closing the switch 12, it is possible to perform switching between the measurement of the contact resistance and the measurement of a biosignal (electroencephalogram or the like), although the details will be described later.

To a + terminal of the amplifier 13, the measurement electrode 14 is connected, and to a − terminal thereof, the ground is connected. The amplifier 13 amplifies and outputs a voltage $V_0$ divided. For the amplifier 13, a general operational amplifier can be used.

The measurement electrode 14 is brought into contact with a living body surface (here, scalp of the user) and is electrically connected thereto. The measurement electrode 14 can be attached to a predetermined position on the scalp of the user, for example, on a position prescribed by the international 10-20 system. Further, a plurality of measurement electrodes 14 can be provided.

The structure of the measurement electrode 14 is not particularly limited but can be a conductive member which is used by being coated with the conductive paste, an elastic member into which a conductive liquid is impregnated, or the like. The conduct resistance between the measurement electrode 14 and the living body surface varies depending on a property of the living body surface or an attachment method but generally falls within a range of approximately tens to hundreds of KΩ.

The neutral electrode 15 is brought into contact with the living body surface and is electrically connected thereto, like the measurement electrode 14. The neutral electrode 15 can be attached to a position less affected by the electroencephalogram, for example, to an earlobe, a temple, or the like. The neutral electrode 15 can have the same structure as the measurement electrode 14.

[Operation of biosignal measurement apparatus] When the switch 12 is turned on with the voltage (hereinafter, referred to as power supply voltage) V1 applied from the voltage supply 10, a minute current I passes through the resistor 11 and the head portion of the user from the measurement electrode 14 and flows to the neutral electrode 15. Therefore, when the sum (hereinafter, referred to as a resistance component of the living body) of the contact resistance between the measurement electrode 14 and the scalp of the user, the resistance of the head portion of the user, and the contact resistance between the scalp of the user and the neutral electrode 15 is represented by a resistance value R2, the following (Expression 1) is established.

$$V_1 = R_1 \cdot I + R_2 I \quad \text{(Expression 1)}$$

Further, the voltage (hereinafter, referred to as detection voltage) $V_0$ detected by the amplifier 13 is expressed by the following (Expression 2).

$$V_0 = I \cdot R_2 \quad \text{(Expression 2)}$$

When the current I is eliminated from (Expression 1) and (Expression 2) described above, the following (Expression 3) is obtained.

$$V_0 = V_1 \cdot R_2 / (R_1 + R_2) \quad \text{(Expression 3)}$$

When (Expression 3) is transformed, the following (Expression 4) is obtained.

$$R_2 = R_1 \cdot V_0 / (V_1 - V_0) \quad \text{(Expression 4)}$$

As described above, it is possible to obtain the resistance value $R_2$ of the resistance component of the living body from the detection voltage $V_0$ detected by the amplifier 13. As shown in (Expression 1) above, the power supply voltage $V_1$ is divided by the resistance value $R_1$ of the resistor 11 and the resistance value $R_2$ of the success component of the living body, so the detection voltage $V_0$ differs depending on the resistance value $R_1$.

Here, in the biosignal measurement apparatus 1 according to the present disclosure, the resistance value $R_1$ of the resistor 11 is set as a logarithmic center value of a range of the measurement value $R_2$ which is intended to be measured. The range of the resistance value $R_2$ which is intended to be measured can be arbitrarily set in accordance with the kind of the measurement electrode 14 used or an attachment method (with or without the conductive paste or the like) to the living body surface. By setting the resistance value $R_1$ in this way, it is possible to expand the measurement range of the resistance value $R_2$ and perform the measurement with high accuracy.

Figure 2:
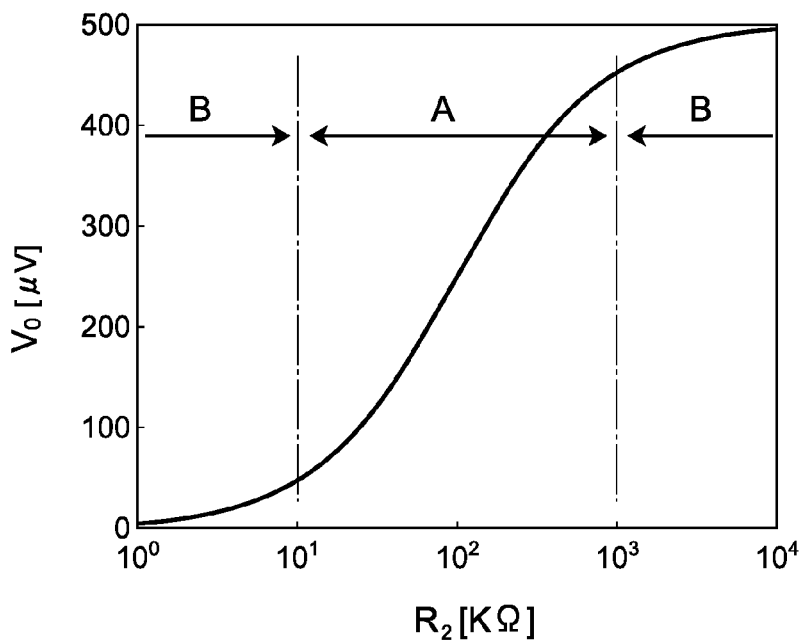
FIG. 2 A graph showing a correlation between a detection voltage and a contact resistance.

Specifically, if the range of the resistance value $R_2$ intended to be measured is 10 KΩ to 1 MΩ, the resistance value $R_1$ is set to 100 KΩ as the logarithmic center value of the range mentioned above. FIG. 2 is a graph showing a correlation between the resistance value $R_2$ of the resistance component of the living body and the detection voltage $V_0$ in the case where the resistance value $R_1$ is set to 100 KΩ, and the amplitude of the voltage supply 10 is set to ±500 µV.

As shown in the figure, the detection voltage $V_0$ shows the largest slope in a range (as indicated by the range A in the figure) in which the resistance value $R_1$ is set as the center and shows a smaller slope in a range (as indicated by the range B in the figure) outside of the range. Specifically, when the range of the resistance value $R_2$ is 10 KΩ to 1 MΩ, the detection voltage $V_0$ varies in a wide range of 100 µV to 400 µV. In contrast, when the range of the resistance value $R_2$ is less than 10 KΩ, the detection voltage $V_0$ varies in the range from 0 to 100 µV, and when the range of the resistance value $R_2$ is more than 1 MΩ, the detection voltage $V_0$ varies in the range from 400 µV to 500 µV, which are relatively narrower ranges. This means that in the range A, even if the resistance value $R_2$ slightly changes, the detection voltage $V_0$ varies, that is, high detection accuracy (resolution) of the resistance value $R_2$ can be obtained.

On the other hand, in the range B, it is impossible to obtain the high detection accuracy. If the resistance value is sufficiently small, the influence of the resistance value $R_2$ given to the biosignal measurement is negligible, and if the resistance value is abnormally large, it can be determined that the measurement electrode 14 is detached from the living body surface. Therefore, in both the cases, if an approximate value of the resistance value $R_2$ can only be obtained, it is unnecessary to obtain a specific value thereof.

That is, in the biosignal measurement apparatus 1 according to the present technology, the resistance value $R_1$ of the resistor 11 is set as the logarithmic center value of the range of the resistance value $R_2$ of the resistance component of the living body which is intended to be measured, with the result that it is possible to measure the resistance value $R_2$ in the necessary range with the high accuracy.

Further, the biosignal measurement apparatus 1 has the structure in which the measurement of the contact resistance and the measurement of the biosignal (electroencephalogram or the like) can be switched by opening and closing the switch 12. Specifically, when the switch 12 is on, the voltage is applied from the voltage supply 10 as described above, and the contact resistance is measured. When the switch 12 is off, the signal of the measurement electrode 14 is amplified by the amplifier 13, and the biosignal is measured.

Figure 3:
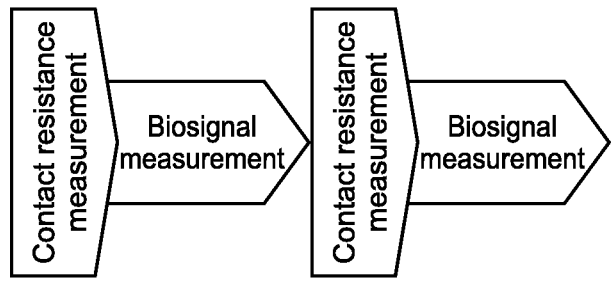
FIG. 3 A schematic diagram showing an operation of the biosignal measurement apparatus.

FIG. 3 is a schematic diagram showing an operation of the measurement of the contact resistance and the measurement of the biosignal by the biosignal measurement apparatus 1. As shown in the figure, before the biosignal is measured, the switch 12 is turned on to measure the contact resistance. If the contact resistance falls within a predetermined range, the switch 12 is turned off, and the measurement of the biosignal can be started. After that, each time a predetermined time period elapses during the measurement of the biosignal, the measurement of the contact resistance is carried out, with the result that the contact resistance can be measured, or detachment of the measurement electrode 14 can be detected, for example.

As described above, in the biosignal measurement apparatus 1 according to this embodiment, it is possible to measure the contact resistance in the necessary range with the high accuracy and measure the biosignal affected by the contact resistance with the high accuracy.

Second Embodiment

A biosignal measurement apparatus according to a second embodiment of the present technology will be described. In this embodiment, description of the same structure as the first embodiment may be omitted in some cases.

[Structure of Biosignal Measurement Apparatus]

Figure 4:
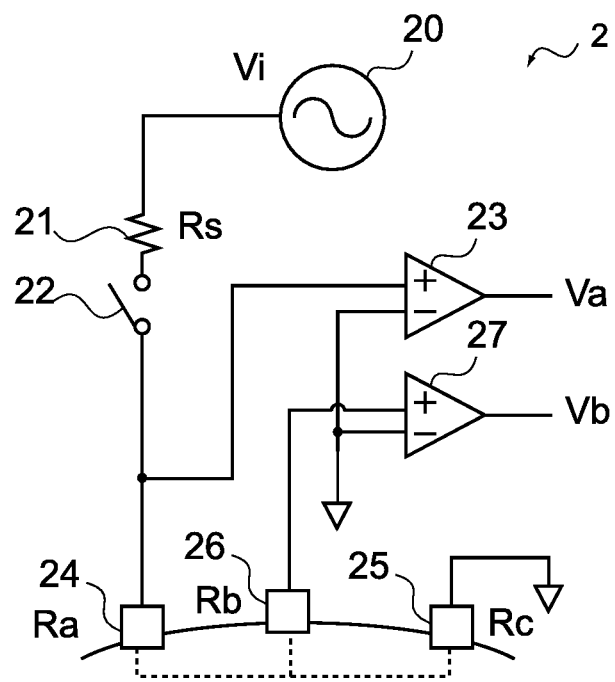
FIG. 4 A schematic diagram showing the structure of a biosignal measurement apparatus according to a second embodiment of the present technology.

FIG. 4 is a schematic diagram showing the structure of a biosignal measurement apparatus 2 according to this embodiment. The biosignal measurement apparatus 2 is an apparatus that is connected to a scalp of the user and measures an electroencephalogram of the user but is not limited to this. The biosignal measurement apparatus 2 can be an apparatus capable of measuring a biosignal generated in a living body, such as an electromyogram, an electrocardiogram, and a body fat percentage. As shown in the figure, the biosignal measurement apparatus 2 includes a voltage supply 20, a resistor 21, a switch 22, an amplifier 23, a measurement electrode 24, a neutral electrode 25, a reference electrode 26, and an amplifier 27.

The voltage supply 20 is connected to the resistor 21, and the resistor 21 is connected to the switch 22. The switch 22 is connected to the measurement electrode 24, and the amplifier 23 is connected between the switch 22 and the measurement electrode 24. The neutral electrode 25 is connected to a ground. The reference electrode 26 is connected to the amplifier 27. As shown in the figure, the measurement electrode 24, the neutral electrode 25, and the reference electrode 26 are attached to the scalp of the user and are electrically connected thereto via a conductive paste or the like.

For the voltage supply 20, a general alternating-current voltage supply can be used. A frequency and a voltage are not particularly limited. For example, the frequency can be set to 10 Hz, and a voltage amplitude can be set to ±500 µV.

The resistor 21 divides the applied voltage with a contact resistance. Hereinafter, a resistance value of the resistor 21 is represented by Rs. As in the first embodiment, the resistance value Rs of the resistor 21 is set as a logarithmic center value of a range of the resistance value of the contact resistance which is intended to be measured with high accuracy.

The switch 22 makes it possible to open and close a circuit. In the biosignal measurement apparatus 2, by opening and closing the switch 22, it is possible to perform switching between the measurement of the contact resistance and the measurement of the biosignal.

To a + terminal of the amplifier 23, the measurement electrode 24 is connected, and to a − terminal thereof, the ground is connected. The amplifier 23 amplifies and outputs a voltage divided. Hereinafter, an amplification factor of the amplifier 23 is represented by an amplification factor A, and an output voltage thereof is represented by a detection voltage Va. For the amplifier 23, a general operational amplifier can be used.

The measurement electrode 24 is brought into contact with a living body surface and is electrically connected thereto. The measurement electrode 24 can be attached to a predetermined position on the scalp of the user, for example, on a position prescribed by the international 10-20 system. Further, a plurality of measurement electrodes 24 can be provided.

The neutral electrode 25 is brought into contact with the living body surface and is electrically connected thereto, like the measurement electrode 24. The neutral electrode 25 can be attached to a position less affected by the electroencephalogram, for example, to an earlobe, a temple, or the like. The neutral electrode 25 can have the same structure as the measurement electrode 24.

The reference electrode 26 is brought into in contact with the living body surface and is electrically connected thereto, like the measurement electrode 24 and the neutral electrode 25. The reference electrode 26 can be attached to a position with little noise, for example, in the vicinity of the top of the head. The reference electrode 26 can have the same structure as the measurement electrode 24.

To a + terminal of the amplifier 27, the reference electrode 26 is connected, and to a − terminal thereof is connected to a ground. The amplifier 27 amplifies and outputs a signal detected by the reference electrode 26. Hereinafter, an amplification factor of the amplifier 27 is represented by an amplification factor B, and an output voltage thereof is represented by a detection voltage Vb. For the amplifier 27, a general operation amplifier can be used.

[Operation of biosignal measurement apparatus] When the switch 22 is turned on with a voltage (hereinafter power supply voltage Vi) applied from the voltage supply 20, a minute current passes through the resistor 21 and the head portion of the user from the measurement electrode 24 and flows to the neutral electrode 25. Therefore, when the contact resistance between the measurement electrode 24 and the scalp of the user is represented by a resistance value Ra, the contact resistance between the reference electrode 26 and the scalp of the user is represented by a resistance value Rb, and the contact resistance between the neutral electrode 25 and the scalp of the user is represented by a resistance value Rc, the following (Expression 5) and (Expression 6) are established.

$$Va=(Ra+Rc)/(Ra+Rc+Rs)\cdot A\cdot Vi \quad \text{(Expression 5)}$$

$$Vb=Rc/(Ra+Rc+Rs)\cdot B\cdot Vi \quad \text{(Expression 6)}$$

When (Expression 5) above is transformed, the following (Expression 7) is obtained, and when (Expression 6) above is transformed, the following (Expression 8) is obtained.

$$(AVi-Va)Ra+(AVi-Va)Rc=VaRs \quad \text{(Expression 7)}$$

$$VbRa+(Vb-BVi)Rc=-VbRs \quad \text{(Expression 8)}$$

(Expression 7) and (Expression 8) above are a simultaneous linear equation with two unknowns, so the resistance value Ra and the resistance value Rc can be obtained.

In this way, it is possible to obtain the resistance value Ra and the resistance value Rc from the detection voltage Va and the detection voltage Vb detected by the amplifier 23 and the amplifier 27, respectively. As shown in (Expression 5) and (Expression 6) above, the power supply voltage Vi is divided by the resistance value Rs of the resistor 21 and the contact resistances of the electrodes, so the detection voltage Va and the detection voltage Vb vary depending on the resistance value Rs.

Here, as in the first embodiment, the resistance value Rs of the resistor 21 is set as the logarithmic center value of the range of the resistance value Ra of the contact resistance which is intended to be measured, thereby making it possible to measure the resistance value Ra in a necessary range with high accuracy.

Further, the biosignal measurement apparatus 2 has the structure in which the measurement of the contact resistance and the measurement of the biosignal (electroencephalogram or the like) can be switched by opening and closing the switch 22. Specifically, when the switch 22 is on, the voltage is applied from the voltage supply 20 as described above to measure the contact resistance. When the switch 22 is off, a difference between signals of the measurement electrode 24 and the reference electrode 26 is amplified (differential amplification) by the amplifier 23 to measure the biosignal.

In the biosignal measurement apparatus 2 according to this embodiment, it is possible to obtain the contact resistances of the electrodes. Therefore, in the case where the contact resistance is abnormally large, that is, in the case where the electrode is detached, it is possible to inform the user of the fact.

Figure 5:
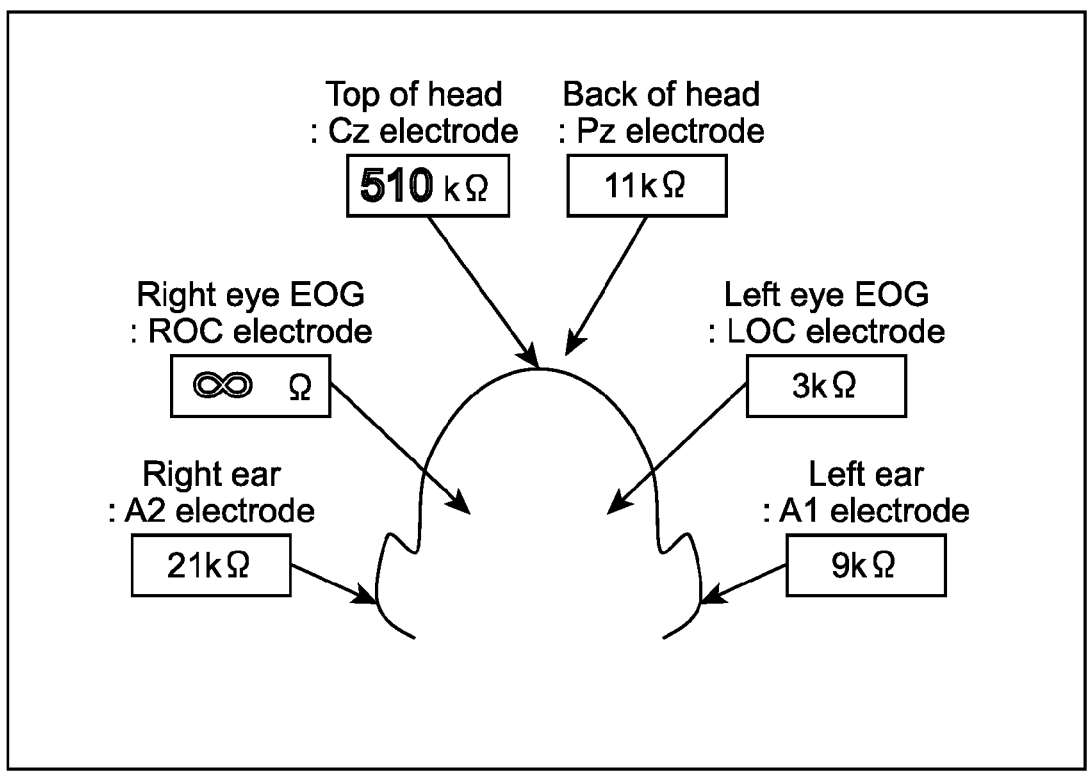
FIG. 5 A schematic diagram showing contact resistance values of electrodes transmitted from the biosignal measurement apparatus and displayed on a display.

For example, the biosignal measurement apparatus 2 can transmit a contact resistance value obtained to a PC (personal computer) by wireless communication or the like. FIG. 5 is a schematic diagram showing contact resistance values of the electrodes displayed on a display of the PC. As shown in the figure, the contact resistance values of the electrodes are displayed, and in the case where the contact resistance value exceeds a threshold value, it is possible to urge the user to improve a contact property of the electrode by an indication, voice, or the like.

As described above, in the biosignal measurement apparatus 2 according to this embodiment, it is possible to measure the contact resistance in the necessary range with the high accuracy and measure the biosignal affected by the contact resistance with the high accuracy.

It should be noted that the present technology can take the following configurations.

(1) A biosignal measurement apparatus, including:
a voltage supply;
a measurement electrode connected to the voltage supply and brought into contact with a living body;
a resistor connected between the voltage supply and the measurement electrode; and
a first amplifier that amplifies a potential between the resistor and the measurement electrode.

(2) The biosignal measurement apparatus according to (1) above, in which
the resistor has a resistance value which is a logarithmic center value of a resistance value range intended to be measured in a resistance value range of a contact resistance between the measurement electrode and the living body.

(3) The biosignal measurement apparatus according to (1) or (2) above, in which
the resistance value range is a range from 10 KΩ to 1 MΩ, both inclusive, and
the resistor has the resistance value of 100 KΩ.

(4) The biosignal measurement apparatus according to any one of (1) to (3) above, further including
a switch capable of opening and closing connection between the resistor and the measurement electrode.

(5) The biosignal measurement apparatus according to any one of (1) to (4) above, further including:
a second amplifier; and
a reference electrode brought into contact with the living body and connected to the second amplifier.

DESCRIPTION OF REFERENCE NUMERALS 1, 2 biosignal measurement apparatus
10, 20 voltage supply
11, 21 resistor
12, 22 switch
13, 23 amplifier
14, 24 measurement electrode
15, 25 neutral electrode
26 reference electrode
27 amplifier

The invention claimed is:
1. A biosignal measurement apparatus, comprising:
a voltage supply;

a resistor positioned between the voltage supply and a switch;

the switch configured to open, in an event a contact resistance between a measurement electrode and a living body is in a determined resistance value range, a connection between the resistor and the measurement electrode for a determined time,
wherein the switch is positioned between the resistor and the measurement electrode;

the measurement electrode connected to the switch, wherein the measurement electrode is configured to be brought into contact with the living body; and a first amplifier positioned between the switch and the measurement electrode, wherein the first amplifier is configured to amplify a potential between the resistor and the measurement electrode.

2. The biosignal measurement apparatus according to claim 1, wherein the resistor has a resistance value which is a logarithmic center value of the determined resistance value range of the contact resistance between the measurement electrode and the living body.

3. The biosignal measurement apparatus according to claim 2, wherein the determined resistance value range is a range from 10 KΩ to 1 MΩ, both inclusive, and the resistor has the resistance value of 100 KΩ.

4. The biosignal measurement apparatus according to claim 1, further comprising:
a second amplifier, wherein a reference electrode is configured to be connected to the second amplifier.

5. The biosignal measurement apparatus according to claim 1, further comprises:
a reference electrode configured to be brought into contact with the living body, wherein in an event the switch is open, the first amplifier is configured to measure a biosignal based on differential amplification of a difference between a signal of the measurement electrode and a signal of the reference electrode.

* * * * *